(12) United States Patent
Castro

(10) Patent No.: US 10,980,643 B2
(45) Date of Patent: *Apr. 20, 2021

(54) JOINT IMPLANT

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 49 days.

This patent is subject to a terminal disclaimer.

(21) Appl. No.: 16/421,737

(22) Filed: May 24, 2019

(65) Prior Publication Data
US 2019/0314171 A1 Oct. 17, 2019

Related U.S. Application Data

(63) Continuation-in-part of application No. 16/097,245, filed as application No. PCT/US2018/025785 on Apr. 3, 2018, now Pat. No. 10,772,738.
(Continued)

(51) Int. Cl.
*A61F 2/44* (2006.01)
*A61F 2/46* (2006.01)
(Continued)

(52) U.S. Cl.
CPC .......... *A61F 2/447* (2013.01); *A61B 17/7002* (2013.01); *A61B 17/7059* (2013.01); *A61F 2/44* (2013.01); *A61F 2/4405* (2013.01); *A61F 2/4455* (2013.01); *A61F 2/4603* (2013.01); *A61F 2/4611* (2013.01); *A61B 17/1671* (2013.01); *A61B 2017/00884* (2013.01); *A61F 2/42* (2013.01); *A61F 2/4606* (2013.01); *A61F 2002/30179* (2013.01); *A61F 2002/30266* (2013.01); *A61F 2002/30364* (2013.01); *A61F 2002/30579* (2013.01); *A61F 2002/30593* (2013.01); *A61F 2002/30622* (2013.01); *A61F 2002/30736* (2013.01); *A61F 2002/30845* (2013.01); *A61F 2002/30995* (2013.01); *A61F 2002/449* (2013.01); *A61F 2002/4627* (2013.01); *A61F 2310/00017* (2013.01); *A61F 2310/00023* (2013.01)

(58) Field of Classification Search
CPC .......... A61F 2/44; A61F 2/4455; A61F 2/447; A61F 2002/30261; A61F 2002/30266; A61F 2002/30271
See application file for complete search history.

(56) References Cited

U.S. PATENT DOCUMENTS 5,683,394 A * 11/1997 Rinner .................. A61F 2/4455
606/86 R
5,800,547 A * 9/1998 Schafer .................. A61F 2/442
623/17.16
(Continued)

FOREIGN PATENT DOCUMENTS

WO WO2007079021 7/2007

*Primary Examiner* — Eduardo C Robert
*Assistant Examiner* — Michelle C Eckman
(74) *Attorney, Agent, or Firm* — Business Patent Law, PLLC

(57) ABSTRACT

A joint implant system adapted for use in joint surgeries. Among other things, the joint implant has an anterior cutting edge and a rotatable cutter supported by a rotatable shaft.

35 Claims, 10 Drawing Sheets

Related U.S. Application Data

(60) Provisional application No. 62/534,155, filed on Jul. 18, 2017.

(51) Int. Cl.
*A61B 17/70* (2006.01)
*A61F 2/30* (2006.01)
*A61F 2/42* (2006.01)
*A61B 17/16* (2006.01)
*A61B 17/00* (2006.01)

(56) References Cited

U.S. PATENT DOCUMENTS

| | | | |
|---|---|---|---|
| 5,800,550 A * | 9/1998 | Sertich | A61F 2/447 623/17.16 |
| 5,888,228 A * | 3/1999 | Knothe | A61F 2/446 623/17.16 |
| 5,980,522 A * | 11/1999 | Koros | A61F 2/446 623/17.11 |
| 6,090,143 A * | 7/2000 | Meriwether | A61F 2/446 623/17.11 |
| 6,371,987 B1 * | 4/2002 | Weiland | A61F 2/4455 623/17.11 |
| 6,767,367 B1 | 7/2004 | Michelson | |
| 6,770,096 B2 | 8/2004 | Bolger | |
| 6,824,564 B2 | 11/2004 | Crozet | |
| 6,981,975 B2 | 1/2006 | Michelson | |
| 7,594,932 B2 | 9/2009 | Aferzon et al. | |
| 7,744,649 B2 * | 6/2010 | Moore | A61F 2/4611 623/17.11 |
| 7,988,709 B2 * | 8/2011 | Clark | A61B 17/7065 606/249 |
| 8,080,062 B2 * | 12/2011 | Armstrong | A61F 2/4465 623/17.11 |
| 8,100,972 B1 * | 1/2012 | Bruffey | A61F 2/447 623/17.11 |
| 8,292,958 B1 * | 10/2012 | Bruffey | A61F 2/4465 623/17.11 |
| 8,366,774 B1 | 2/2013 | Bruffey et al. | |
| 8,382,843 B2 | 2/2013 | Laurence et al. | |
| 8,545,562 B1 * | 10/2013 | Materna | A61F 2/4465 623/17.11 |
| 8,617,245 B2 * | 12/2013 | Brett | A61F 2/4611 623/17.16 |
| 8,795,368 B2 | 8/2014 | Trieu et al. | |
| 8,864,829 B1 * | 10/2014 | Bruffey | A61F 2/442 623/17.11 |
| D742,517 S * | 11/2015 | Schifano | D24/155 |
| 9,198,764 B2 * | 12/2015 | Greenberg | A61F 2/447 |
| 9,198,774 B2 * | 12/2015 | Pisharodi | A61F 2/447 |
| 9,517,144 B2 * | 12/2016 | McAtamney | A61F 2/30749 |
| 9,539,110 B2 | 1/2017 | Bergey | |
| 9,566,165 B2 * | 2/2017 | Lee | A61F 2/442 |
| 9,642,721 B2 * | 5/2017 | Patterson | A61F 2/4455 |
| 9,987,142 B2 * | 6/2018 | McConnell | A61F 2/447 |
| 10,159,582 B2 | 12/2018 | Gamache | |
| 10,517,651 B1 * | 12/2019 | Weaver | A61B 90/06 |
| 10,548,740 B1 * | 2/2020 | Abdou | A61F 2/447 |
| 2002/0120334 A1 * | 8/2002 | Crozet | A61B 17/86 623/17.11 |
| 2003/0149484 A1 * | 8/2003 | Michelson | A61F 2/4611 623/17.16 |
| 2003/0181981 A1 * | 9/2003 | Lemaire | A61F 2/4455 623/17.11 |
| 2003/0187436 A1 * | 10/2003 | Bolger | A61B 17/025 623/17.11 |
| 2004/0088054 A1 * | 5/2004 | Berry | A61F 2/4455 623/17.11 |
| 2005/0033429 A1 * | 2/2005 | Kuo | A61F 2/447 623/17.11 |
| 2005/0049590 A1 * | 3/2005 | Alleyne | A61F 2/442 623/17.11 |
| 2005/0143822 A1 * | 6/2005 | Paul | A61F 2/4455 623/17.16 |
| 2006/0095136 A1 * | 5/2006 | McLuen | A61F 2/4455 623/23.47 |
| 2006/0224241 A1 * | 10/2006 | Butler | A61F 2/446 623/17.15 |
| 2007/0055378 A1 * | 3/2007 | Ankney | A61F 2/4425 623/17.15 |
| 2007/0118220 A1 * | 5/2007 | Liu | A61F 2/447 623/17.11 |
| 2007/0162130 A1 * | 7/2007 | Rashbaum | A61F 2/4611 623/17.11 |
| 2007/0270961 A1 | 11/2007 | Ferguson | |
| 2008/0027550 A1 * | 1/2008 | Link | A61B 17/1671 623/17.16 |
| 2008/0132949 A1 * | 6/2008 | Aferzon | A61F 2/4425 606/246 |
| 2008/0255501 A1 * | 10/2008 | Hogendijk | A61F 2/30721 604/64 |
| 2008/0255666 A1 * | 10/2008 | Fisher | A61B 17/7064 623/17.16 |
| 2009/0054988 A1 * | 2/2009 | Hess | A61B 17/7065 623/17.16 |
| 2009/0099601 A1 * | 4/2009 | Aferzon | A61F 2/4455 606/246 |
| 2009/0164020 A1 * | 6/2009 | Janowski | A61F 2/4465 623/17.16 |
| 2009/0240333 A1 * | 9/2009 | Trudeau | A61F 2/4684 623/17.13 |
| 2009/0265007 A1 * | 10/2009 | Colleran | A61F 2/4465 623/17.16 |
| 2010/0016974 A1 * | 1/2010 | Janowski | A61F 2/442 623/17.16 |
| 2010/0094425 A1 * | 4/2010 | Bentley | A61B 17/0482 623/17.16 |
| 2010/0185289 A1 * | 7/2010 | Kirwan | A61F 2/4455 623/17.11 |
| 2011/0035007 A1 * | 2/2011 | Patel | A61F 2/4611 623/17.11 |
| 2011/0112587 A1 * | 5/2011 | Patel | A61F 2/4611 606/86 A |
| 2011/0166660 A1 * | 7/2011 | Laurence | A61F 2/4455 623/17.16 |
| 2011/0208311 A1 * | 8/2011 | Janowski | A61F 2/4611 623/17.16 |
| 2012/0046748 A1 * | 2/2012 | Weiman | A61F 2/44 623/17.16 |
| 2012/0150300 A1 * | 6/2012 | Nihalani | A61F 2/442 623/17.16 |
| 2012/0277864 A1 * | 11/2012 | Brodke | A61F 2/4611 623/17.16 |
| 2012/0277865 A1 * | 11/2012 | Trieu | A61F 2/442 623/17.16 |
| 2012/0277868 A1 * | 11/2012 | Walters | A61F 2/442 623/17.16 |
| 2012/0303124 A1 * | 11/2012 | McLuen | A61F 2/447 623/17.16 |
| 2013/0018465 A1 * | 1/2013 | Yue | A61F 2/447 623/17.12 |
| 2013/0018472 A1 * | 1/2013 | Yue | A61F 2/447 623/17.16 |
| 2013/0073044 A1 * | 3/2013 | Gamache | A61F 2/447 623/17.16 |
| 2013/0079880 A1 * | 3/2013 | Wolters | A61B 17/7068 623/17.16 |
| 2013/0197647 A1 * | 8/2013 | Wolters | A61F 2/446 623/17.16 |
| 2013/0253649 A1 * | 9/2013 | Davis | A61F 2/446 623/17.16 |
| 2013/0261746 A1 * | 10/2013 | Linares | A61F 2/442 623/17.16 |
| 2013/0261747 A1 * | 10/2013 | Geisert | A61F 2/4455 623/17.16 |
| 2013/0268076 A1 * | 10/2013 | Carlson | A61F 2/447 623/17.16 |

(56) References Cited

U.S. PATENT DOCUMENTS

| | | | |
|---|---|---|---|
| 2013/0282125 A1* | 10/2013 | Etminan | A61F 2/4611 623/17.16 |
| 2013/0338776 A1* | 12/2013 | Jones | A61F 2/4611 623/17.16 |
| 2014/0052260 A1 | 2/2014 | McKenny et al. | |
| 2014/0058517 A1* | 2/2014 | Sabatino | A61F 2/4425 623/17.16 |
| 2014/0094917 A1* | 4/2014 | Salerni | A61F 2/447 623/17.16 |
| 2014/0094918 A1* | 4/2014 | Vishnubholta | A61F 2/442 623/17.16 |
| 2014/0100663 A1* | 4/2014 | Messerli | A61F 2/442 623/17.16 |
| 2014/0114416 A1* | 4/2014 | Zimmerman | A61F 2/44 623/17.16 |
| 2014/0114421 A1 | 4/2014 | Ullrich, Jr. et al. | |
| 2014/0121773 A1* | 5/2014 | Patel | A61F 2/4455 623/17.16 |
| 2014/0172104 A1* | 6/2014 | Dugal | A61F 2/4465 623/17.16 |
| 2015/0045893 A1* | 2/2015 | Dinville | A61F 2/44 623/17.16 |
| 2015/0100127 A1* | 4/2015 | Bal | A61F 2/447 623/17.16 |
| 2015/0127107 A1* | 5/2015 | Kim | A61F 2/4611 623/17.16 |
| 2015/0173917 A1* | 6/2015 | Radcliffe | A61F 2/4455 623/17.16 |
| 2015/0265416 A1 | 9/2015 | Aferzon et al. | |
| 2015/0305880 A1* | 10/2015 | Kim | A61F 2/4465 623/17.16 |
| 2016/0000578 A1* | 1/2016 | Bae | A61F 2/4455 623/17.16 |
| 2016/0038299 A1* | 2/2016 | Chen | A61F 2/4455 623/17.16 |
| 2016/0045326 A1* | 2/2016 | Hansen | A61F 2/447 623/17.16 |
| 2016/0113781 A1* | 4/2016 | Laurence | A61B 17/68 623/17.16 |
| 2016/0199190 A1* | 7/2016 | Sharifi-Mehr | A61F 2/44 623/17.12 |
| 2016/0235546 A1* | 8/2016 | Cheng | A61F 2/4465 |
| 2016/0302941 A1* | 10/2016 | Reiley | A61B 17/1615 |
| 2016/0374831 A1* | 12/2016 | Duffield | A61F 2/4611 623/17.16 |
| 2017/0056179 A1* | 3/2017 | Lorio | B22F 3/1055 |
| 2017/0056192 A1* | 3/2017 | Buss | A61F 2/447 |
| 2017/0095352 A1* | 4/2017 | Bruffey | A61F 2/4465 |
| 2017/0135822 A1* | 5/2017 | Bender | A61F 2/447 |
| 2017/0165082 A1* | 6/2017 | Faulhaber | A61F 2/447 |
| 2017/0181863 A1* | 6/2017 | Bjork | A61F 2/4611 |
| 2017/0311991 A1* | 11/2017 | Kim | A61B 17/7067 |
| 2017/0340453 A1* | 11/2017 | Kaufmann | A61F 2/4455 |
| 2017/0360571 A1* | 12/2017 | Mesiwala | A61F 2/4611 |
| 2018/0104068 A1* | 4/2018 | Sack | A61F 2/4465 |
| 2018/0110627 A1* | 4/2018 | Sack | A61F 2/4465 |
| 2018/0296359 A1* | 10/2018 | Sack | A61F 2/4465 |
| 2019/0224017 A1* | 7/2019 | Grim | A61F 2/442 |
| 2019/0314171 A1* | 10/2019 | Castro | A61F 2/447 |
| 2019/0350673 A1* | 11/2019 | Kieser | A61F 2/447 |
| 2020/0046513 A1* | 2/2020 | Castro | A61B 17/7059 |
| 2020/0179133 A1* | 6/2020 | Ryan | A61F 2/442 |
| 2020/0179135 A1* | 6/2020 | Castro | A61F 2/4618 |

\* cited by examiner

JOINT IMPLANT

Applicant claims priority to U.S. Nonprovisional patent application entitled—Joint Arthrodesis System—, Ser. No. 16/097,245, filed Oct. 27, 2018 that claimed priority to PCT Application entitled—Joint Arthrodesis System—, Serial No. PCT/US2018/025785, filed Apr. 3, 2018 that claimed priority to U.S. provisional Patent Application entitled—Joint Arthrodesis System—, Ser. No. 62/534,155, filed Jul. 18, 2017.

BACKGROUND OF THE INVENTION

A. Field of the Invention

The present invention is a joint arthrodesis system. Among other things, the implant of the current system has a cutting edge as well as a rotatable cutter. Select preferred embodiments of the current implant can be provided with a socket and bearing that allow a rotatable shaft to be detached/reattached from the socket.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 6,770,096-Bolger, et al. that discloses an interbody spinal stabilization cage and spinal stabilization method; 2) U.S. Pat. No. 6,824,564-Crozet that discloses a two-part intersomatic implant; 3) U.S. Pat. No. 6,981,975-Michelson that discloses a method for inserting a spinal fusion implant having deployable bone engaging projections; 4) U.S. Pat. No. 7,594,932-Aferzon, et al. discloses an apparatus for anterior intervertebral spinal fixation and fusion; 5) U.S. Pat. No. 8,366,774-Bruffey, et al. that discloses an apparatus for anterior intervertebral spinal fixation and fusion; 6) U.S. Pat. No. 8,382,843-Laurence, et al. that discloses an intervertebral implant with blades for connecting to adjacent vertebral bodies; 7) U.S. Pat. No. 9,539,110-Bergey that discloses an interbody prosthetic device with compound-arc, blade anchor; 8) US Published Patent Application No. 20030187435-Bolger, et al. that an interbody spinal stabilization cage and spinal stabilization method; 9) US Published Patent Application 2007011820-Liu, et al. that discloses a vertebral implant for promoting arthrodesis of the spine; 10) US Published Patent Application No. 20070270961-Ferguson that discloses a spinal implant deployable with retractable barbs; 11) US Published Patent Application No. 20080027550-Link, et al. that discloses a cervical intervertebral disc prosthesis comprising an anti-dislocation device and instruments; 12) US Published Patent Application No. 20140094918-Vishnubholta, et al. that discloses a stand-alone interbody fixation system; 13) US Published Patent Application No. 20140114421-Titan Spine, LLC that discloses an interbody spinal implant having a roughened surface topography; 14) US Published Patent Application No. 20140121773-Patel, et al. that discloses a stand-alone interbody fixation system; 15) US Published Patent Application No. 20150265416-Aferzon, et al. that discloses an apparatus for anterior intervertebral spinal fixation and fusion; 16) US Published Patent Application No. 20160374831-Duffield, et al. that discloses an interbody fusion device and system for implantation; and 17) WIPO Published Patent Application No. 2007/079021-Aferzon, et al. that discloses an apparatus for anterior intervertebral spinal fixation and fusion.

Among other things, none of the above listed references disclose a framework or a biocompatible construction that include comprising: an anterior side comprising a cutting edge; a rotatable shaft extending between the anterior side and the surgeon facing side; cutters connected to first and second arms connected with the rotatable shaft where the cutters are adapted to cut in a clockwise or counterclockwise direction; a socket and bearing that allow the rotatable shaft to be detached from the biocompatible construction; or a joint implant comprising a biocompatible construction comprising: a first trapezoidal surface comprising a first aperture therein and a first two margins of equal length; a second trapezoidal surface opposed from the first trapezoidal surface; the second trapezoidal surface comprising a second aperture therein and a second two margins of equal length; an anterior side extending between the trapezoidal surfaces; the anterior side comprising a cutting edge; a surgeon facing side comprising a bearing; the surgeon facing side extending between the trapezoidal surfaces; and a rotatable shaft extending from the cutting edge into the bearing; the rotatable shaft comprising: a conduit extending through the length of the rotatable shaft; the conduit defined by the inward face of the shaft's cylindrical wall; one or more windows, positioned in the cylindrical wall; each window exposing the conduit to a surgically created cavity external from the joint implant; and first and second arms connected with the rotatable shaft; the first and second arms supporting first and second cutters comprising one or more blades, wherein on rotation of the shaft, the blades are adapted to cut in a clockwise or counterclockwise direction.

SUMMARY OF THE INVENTION

The more tools or instruments inserted into a surgical field, the greater the possibility that technique error may result in patient injury. Due to the simplicity of the current joint arthrodesis system, a number of surgical tools required and steps associated with performing prior state-of-the-art fusions can be eliminated. The arthrodesis procedures, among other uses, can be performed in the cervical spine, sacroiliac joint, ankle, hand or other similar joints.

One of the currently available state-of-the art techniques for cervical fusions is the DTRAX system. The DTRAX spinal system uses five instruments, a working cannula, and numerous steps. A working cannula with a chisel is used to breach the desired posterior facet joint. Once in position, the chisel is removed and a broach is inserted through the working cannula. The broach is advanced and retracted several times in order to remove the cartilaginous end-plates. After the broach is removed from the working cannula, a drill is inserted. After drilling is completed, a second rasp is placed to decorticate the posterior cortex. After the use of the second rasp is completed, the fixation device (filled with graft material) is inserted through the working cannula into the joint. Additional graft material is then impacted behind the implant.

Current state-of-the-art sacroiliac surgical procedures require a fusion device that is either inserted from a posterior or lateral approach. Applicant's understanding is: there are fusion devices for use with either the posterior approach or the lateral approach, but the same fusion device is incapable for use with both the posterior and the lateral approaches. Many of the current sacroiliac fusion procedures require the use of working cannulas, numerous broaches, rasps, drills and other devices that tend to complicate the surgical procedure. Applicant's current joint arthrodesis system can accomplish sacroiliac fusions through either a posterior or lateral approach with fewer surgical tools and steps.

Unlike other joint arthrodesis systems, the present system's joint arthrodesis implant includes a cutting edge and one or more rotatable cutters including one or more blades connected to a rotatable shaft. Among other things, it is believed that the cutters can assist with the postoperative stabilization of the joint implant. In accordance with the current invention, rotation of a blade about 90 degrees allows the blade to extend beyond the joint implant's framework and penetrate adjacent cartilage and bone. Select preferred embodiments of the current invention include a socket and bearing that allow the rotatable shaft to be detached/reattached from socket. Detachment/reattachment of the rotatable shaft allows the surgeon to move of the rotatable shaft along its longitudinal axis.

An aspect of the present invention is to provide a joint implant with an anterior side having a cutting edge.

Still another aspect of the present invention is to provide a joint implant with a rotatable shaft extending from the anterior side into the surgeon facing side.

It is still another aspect of the present invention to provide a joint implant with one or more rotatable cutters affixed to the shaft, where each cutter can include one or more blades.

Yet still another aspect of the present invention is to provide a joint implant where rotation of the rotatable cutter causes one or more of the cutters to extend beyond the framework.

Still another aspect of the present invention is to provide a joint implant with rotatable cutters for cutting in the clockwise or counterclockwise directions.

Yet another aspect of the present invention is to provide a joint implant with a socket and bearing adapted to engage the rotatable shaft.

It is still another aspect of the present invention to provide a joint implant where the rotatable shaft can be detached from the joint implant without compromising the stability of the implant remaining in the surgically created cavity.

Still another aspect of the present invention is to provide edges on the cutting arms that can assist with the removal of cartilage, exposure of subcortical bone and/or morselization of graft material.

Yet another aspect of the present invention is to provide a joint implant that, after insertion into the surgically created opening, provides distraction.

Still another aspect of the present invention is to provide a joint implant that after insertion into the posterior cervical facet joint, the distraction can indirectly provide some neuroforaminal decompression.

It is still another aspect of the present invention to provide a joint implant with a framework or biocompatible construction that can lessen any joint implant subsidence.

Yet another aspect of the present invention is to provide a joint implant that includes surface treatments. Surface treatments can improve fixation of the joint implant, and it is believed that when the joint implant is inserted at an angle perpendicular to the joint surfaces, surface treatments significantly improve fusion.

Yet still another aspect of the present invention is to provide a rotatable shaft including a conduit and one or more windows for delivery of biocompatible instruments, compositions or substances.

A preferred embodiment of the current invention can be described as a joint implant comprising a framework; the framework comprising: a) a longitudinal axis measured in a coexisting or parallel direction of a longest dimension of the framework; b) openings outward from the longitudinal axis; c) an anterior side comprising a cutting edge; d) a surgeon facing side at an end opposite the anterior side; the surgeon facing side comprising one or more apertures; e) a rotatable shaft extending about the longitudinal axis and between the anterior side and the surgeon facing side; f) a first arm connected with the shaft; the first arm supporting a first cutter comprising one or more blades, wherein on rotation of the shaft, the blades are adapted to cut when rotated in a clockwise or counterclockwise direction; and g) a second arm connected with the shaft; the second arm supporting a second cutter comprising one or more blades, wherein on rotation of the shaft, the blades are adapted to cut when rotated in a clockwise or counterclockwise direction.

Another preferred embodiment of the current invention can be described as a joint implant comprising a framework; the framework comprising: a) a longitudinal axis measured in a coexisting or parallel direction of a longest dimension of the framework; b) openings outward from the longitudinal axis; c) an anterior side comprising a cutting edge; d) a surgeon facing side at an end opposite the anterior side; the surgeon facing side comprising at least one aperture; e) a rotatable shaft extending along the longitudinal axis and between the anterior side and the surgeon facing side; f) first and second arms connected with the shaft; the first and second arms supporting first and second cutters comprising one or more blades, wherein on rotation of the shaft, the blades are adapted to cut when rotated in a clockwise or counterclockwise direction; and g) one or more connectors connected to the surgeon facing side, wherein each connector is adapted to engage an insertion device.

Still another preferred embodiment of the current invention can be described as a joint implant comprising a biocompatible construction with a longitudinal axis measured in a coexisting or parallel direction of a longest dimension of the biocompatible construction; the biocompatible construction comprising: a) openings outward from the longitudinal axis; b) an anterior side comprising: i) a cutting edge; ii) and a socket; c) a surgeon facing side, opposite the anterior side, comprising a bearing including opposed first and second gaps perpendicular to the longitudinal axis; d) a rotatable shaft engaging the socket and extending along the longitudinal axis from the socket through the bearing, wherein said rotatable shaft is detachable from the socket and the bearing; and e) first and second arms connected with the shaft; the first and second arms supporting first and second cutters comprising one or more blades, wherein on rotation of the shaft, the blades are adapted to cut in a clockwise or counterclockwise direction.

Yet another preferred embodiment of the current invention can be described as a joint implant comprising a biocompatible construction with a longitudinal axis spanning a longest dimension of the biocompatible construction; the biocompatible construction comprising: a) openings outward from the longitudinal axis; b) an anterior side comprising: i) a cutting edge; ii) and a socket; c) a surgeon facing side, opposite the anterior side, comprising a bearing comprising first and second gaps; d) a rotatable shaft, extending along or parallel to said longitudinal axis, engaging the socket and extending into the bearing, wherein the rotatable shaft is detachable from the biocompatible construction; and e) first and second arms connected with the shaft; the first and second arms supporting first and second cutters comprising one or more blades, wherein on rotation of the shaft, the blades are adapted to cut in a clockwise or counterclockwise direction.

Yet still another preferred embodiment of the current invention can be described as a joint implant comprising a biocompatible construction with a longitudinal axis spanning a longer dimension of said biocompatible construction; the biocompatible construction comprising: a) openings outward from the longitudinal axis; b) an anterior side comprising: i) a cutting edge; and ii) a socket; c) a surgeon facing side comprising a bearing; d) a rotatable shaft, extending along the longitudinal axis, engaging the socket and the bearing, wherein the rotatable shaft is detachable from the biocompatible construction; and e) first and second arms connected with the shaft; the first and second arms supporting first and second cutters comprising one or more blades, wherein on rotation of the shaft, the blades are adapted to cut in a clockwise or counterclockwise direction.

Still another preferred embodiment of the current invention can be described as a joint implant comprising a biocompatible construction with a longitudinal axis spanning a longer dimension of the biocompatible construction; the biocompatible construction comprising: a) a first trapezoidal surface comprising a first aperture therein and a first two margins of equal length; b) a second trapezoidal surface opposed from the first trapezoidal surface; the second trapezoidal surface comprising a second aperture therein and a second two margins of equal length; c) an anterior side extending between the trapezoidal surfaces; the anterior side comprising a cutting edge and an orifice extending through the anterior side and the cutting edge; d) a surgeon facing side comprising a bearing; the surgeon facing side extending between the trapezoidal surfaces; and e) a rotatable shaft extending from the orifice into the bearing; the rotatable shaft comprising: i) a conduit extending through a length of the rotatable shaft; the conduit defined by an inward face of the rotatable shaft's cylindrical wall; ii) one or more windows, positioned on the cylindrical wall; each window exposing the conduit to a surgically created cavity external from the joint implant; and iii) first and second arms connected with the rotatable shaft; the first and second arms supporting first and second cutters comprising one or more blades, wherein on rotation of the shaft, the blades are adapted to cut in a clockwise or counterclockwise direction.

Yet another preferred embodiment of the current invention can be described as a joint implant comprising a biocompatible construction with a longitudinal axis spanning a longer dimension of the biocompatible construction; the biocompatible construction comprising: a) openings outward from the longitudinal axis; b) an anterior side comprising a cutting edge and an orifice extending through the anterior side; c) a surgeon facing side comprising a bearing, wherein the anterior side has a lesser cross-sectional area than a cross-sectional area of the surgeon facing side; and d) a rotatable shaft extending from the orifice into the bearing; the rotatable shaft comprising: i) a conduit extending through a length of the rotatable shaft; the conduit defined by an inward face of the rotatable shaft's cylindrical wall; ii) one or more windows, positioned on the cylindrical wall; each window exposing the conduit to a surgically created cavity external from the joint implant; and iii) first and second arms connected with the rotatable shaft; the first and second arms supporting first and second cutters comprising one or more blades, wherein on rotation of the shaft, the blades are adapted to cut in a clockwise or counterclockwise direction.

It is the novel and unique interaction of these simple elements which creates the system within the ambit of the present invention. Pursuant to the Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Figure 1:
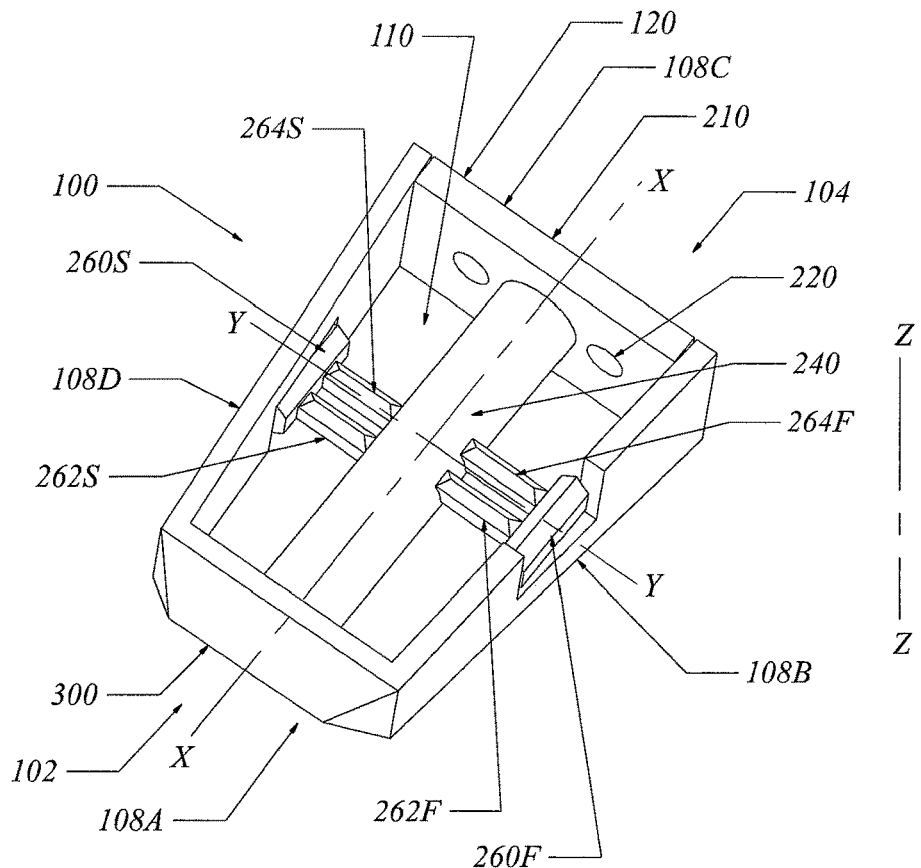
FIG. 1 is a perspective of a preferred embodiment of the joint implant (100) utilized in the present system.

Although the disclosure hereof is detailed to enable those skilled in the art to practice the invention, the embodiments published herein merely exemplify the present invention.

As used herein, with respect to the joint implant: 1) "anterior" of the joint implant means the side of the implant most distant from the surgeon and 2) "posterior or surgeon-facing side" of the joint implant means the side of the implant nearest the surgeon.

In the most general sense, the present invention is a joint arthrodesis system where an implant is surgically inserted into a joint space. The current implant can be useful for surgeries that can assist in stabilizing injured, deformed and or degenerative joints. Preferred embodiments of the current invention can be employed with ankle, cervical, hand, sacroiliac or other orthopaedic procedures. It appears that the present system is particularly useful for posterior cervical fusions and sacroiliac joint fusions. However, the current invention can also be used to fuse the tibia to the talus, the talus to the calcaneus, and metacarpals to the phalanges.

Preferred embodiments of the current joint implants can be manufactured of titanium alloys, stainless steel, resorbable polymers, non-resorbable polymers or any other composition acceptable in the art. Meeting a long felt but unfilled need in the orthopaedic surgical arts, the novel and unique structures of the present combinations allow the surgical team to, among other things, simplify previous procedures.

The present invention has a cutting edge and a rotatable cutter including one or more blades. The cutting edge of the implant's framework is capable of dissecting through adipose, muscle and/or joint capsule tissues. The rotatable cutter of the implant is capable of cutting cartilage and bone and can be associated with the creation of the surgical cavity. Further, the rotatable cutter can remove cartilage, expose subcortical bone and/or morselize graft material. The combination of the cutting edge(s) and rotatable cutter of the current joint implant meet long felt but unfilled needs in the orthopedic surgical arts: among other things, these novel and unique structures allow the surgeon to simplify the previous operating procedures utilized for posterior cervical, sacroiliac, and other joint fusions.

Devices that insert osteogenic and/or other substances into the interior volume of the implant can be used with the present invention. The current joint arthrodesis system is also compatible with flexible drills, fiber optics, vacuums, one or more cannulas and one or more devices for inserting the joint implant. Combinations of one or more of the before identified ancillary devices and the current joint implant can assist with the creation and healing of the surgical wound.

Openings of the current joint implant increase the probability of the osteogenic materials and/or arthrodesis accelerating substances procuring a blood supply. And it is believed that increasing the blood supply to the osteogenic materials held by the joint implant or implant increases the probability of successful fusion. Introduction of osteogenic and other biocompatible substances into the implant can hasten the healing of the surgical wound.

FIG. 1 is a perspective of a preferred embodiment of the joint implant (100) utilized in the present system. Joint implant or implant (100) has a framework that includes an anterior side (102), surgeon facing or posterior side (104) and a plurality of sides (108A-D). Sides (108A-D) are provided with opening (110) that, among other things, allows the implant's blades to rotate. When surgical parameters require, osteogenic and/or other biocompatible substances can also be placed into the internal volume of implant (100).

With respect to this application, the longitudinal axis of joint implant (100) is measured along axis X-X. Axis X-X can correspond with shaft (240) or in some preferred embodiments shaft (240) can be offset from axis X-X. Width of implant (100) is measured along axis Y-Y or an axis parallel to axis Y-Y shown in FIG. 1. Height of joint implant is measured along axis Z-Z or an axis parallel to axis Z-Z of the joint implant's framework.

Within the scope of the current invention, select embodiments of implant (100) have a length greater than a width. In select preferred embodiments, the width of implant (100) is greater than the height of implant (100). In other preferred embodiments of implant (100), the height of implant (100) is greater than the width of implant (100). The inward sides of anterior side (102), posterior side (104) and sides (108A-D) facing longitudinal axis X-X create an available inner volume of implant (100) which can receive osteogenic as well as other substances.

Sides (108A-108D) are positioned outward from joint implant's (100) longitudinal axis X-X. Select preferred embodiments of implant (100) are provided with a cross-section distant from anterior side (102) that has a greater cross-sectional area than the anterior side (102). As disclosed herein, cross-sections are determined perpendicular to the longitudinal axis X-X of the implant's framework. Anterior side (102) of implant (100) is provided with cutting edge (300) as will be more specifically enabled below. In some preferred embodiments, cutting edge (300) can be integral with anterior side (102) of joint implant (100). Attached to shaft (240) are arms (262F, 262S) supporting cutters (260F, 260S). Although as shown in FIG. 1, cutters (260F, 260S) are supported by two arms (262F, 262S), in select preferred embodiments, cutters (260F, 260S) can be supported by a single arm (262F, 262S). Additionally, some preferred embodiments of cutters (260F, 260S) can be provided with one or more sharp edges (264F, 264S) that can assist cutters (260F, 260S) with the remove cartilage, expose subcortical bone and/or morselize graft material.

Posterior side (104) of implant (100) includes cross-sectional area (120). Preferred embodiments of joint implant (100) can be provided with plate (210) where at least a portion the plate (210) is perpendicular to longitudinal axis X-X. Plate (210) is seated within cross-sectional area (120) of surgeon facing side (104) and affixed to implant (100). Preferred embodiments of plate (210) are provided with one or more apertures (220) that can be utilized with one or more tools associated with the surgery.

Figure 2:
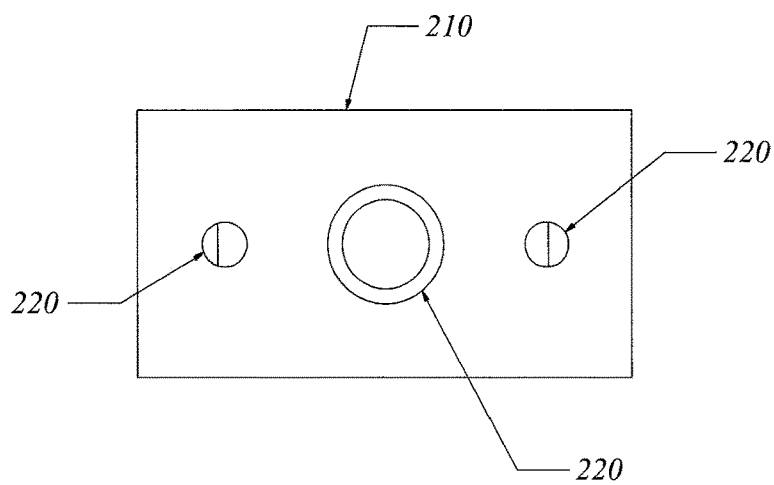
FIG. 2 is a frontal view of plate (210) seated in cross-sectional area (120) of surgeon facing side (104) of implant (100).

FIG. 2 is a frontal view of plate (210) seated in cross-sectional area (120) of surgeon facing side (104) of implant (100). As shown, cross-sectional area is provided with a plurality of openings (220).

Figure 3:
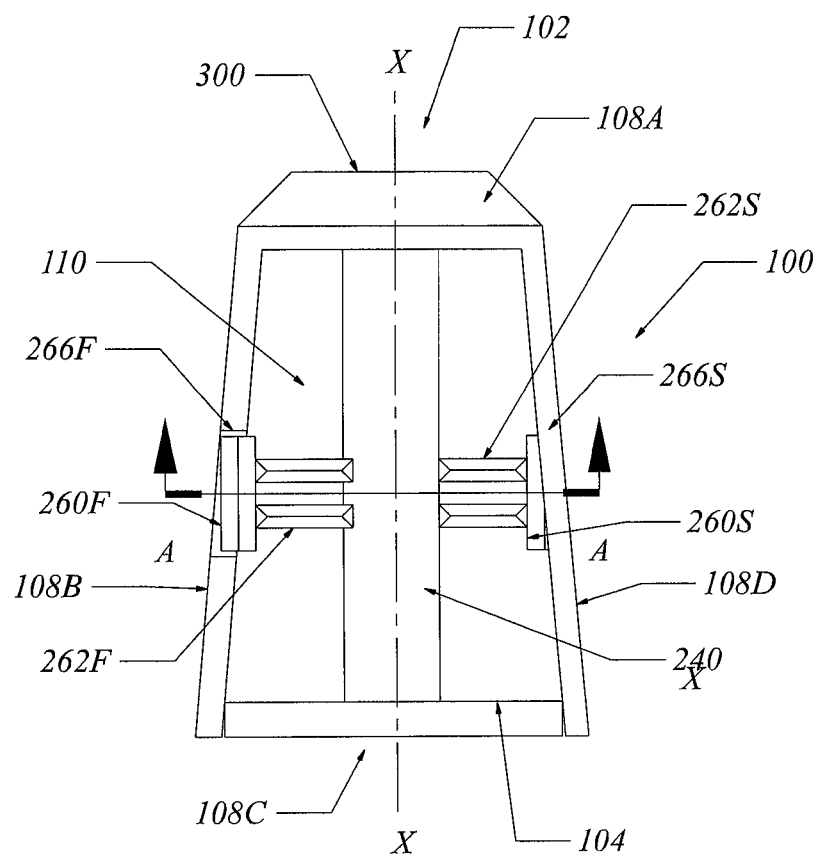
FIG. 3 is a top view of a preferred embodiment of implant (100).

FIG. 3 is a top view of implant (100), where implant is shown in its subcutaneous surgical wound creation mode. Shaft (240) is connected with anterior end (102) and posterior side (104) in any manner acceptable in the art. Proximate shaft (240) is opening (110) and sides (108A-108D). First arms (262F) attach first cutter (260F) to shaft (240). Second arms (262S) attach second cutter (260S) to shaft (240). Cutters (260F and 260S) can be provided with blades that cut in both the clockwise and counterclockwise directions when shaft (240) is rotated. Side (108B) is provided with recess (266F) capable of receiving cutter (260F). Side (108D) is provided with recess (266S) capable of receiving cutter (260S). As shown in FIG. 3, recess (266F) is located on the superior side of lengthwise side (108B) and recess (266S) is positioned on the inferior side of side (108D).

Figure 4:
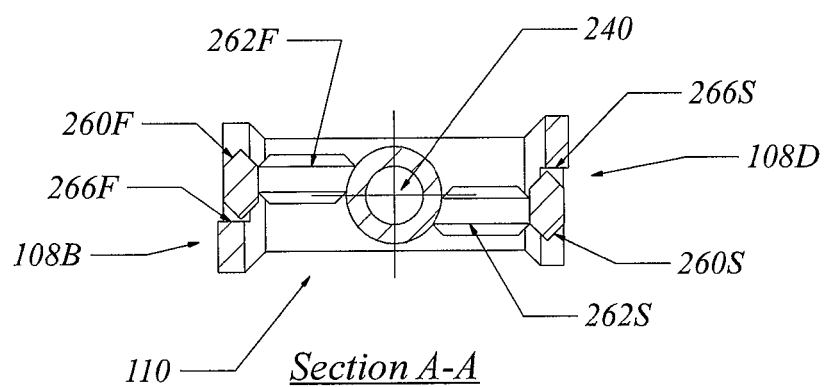
FIG. 4 is a frontal view cross-section of implant (100) along section A-A as seen from the posterior side (104).

FIG. 4 is a frontal view cross-section of implant (100) along section A-A as seen from the posterior side (104). Cutter (260F) is received in recess (266F) of lateral side (108B) and arms (262F) attach cutter (260F) to shaft (240). Cutter (260S) is received in recess (266S) of lateral side (108D) and arms (262S) attach cutter (260S) to shaft (240).

Within the scope of the current invention, cutters (260F, 260S) can be supported by a single arm (262F, 262S). And when surgical parameters require, implant (100) is engineered with only a single cutter (260F).

Figure 5:
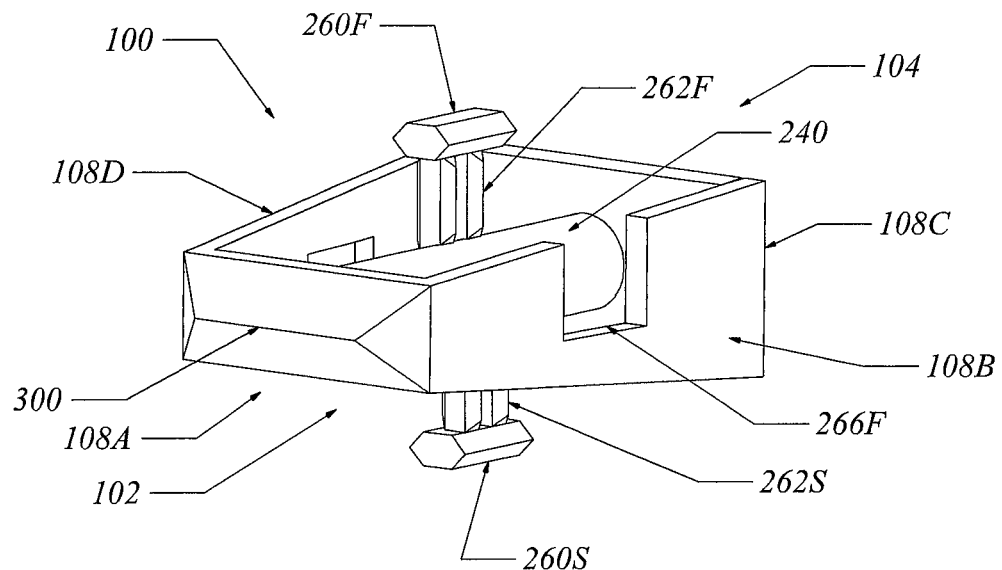
FIG. 5 is a perspective of a preferred embodiment of implant (100).

FIG. 5 is a perspective of a preferred embodiment of implant (100). Shaft (240) extends from cutting edge (300) toward surgeon facing side (104) of implant (100). As shown in FIG. 5, shaft (240) has rotatable arms (262F, 262S) carrying cutters (260F, 260S) such that rotation of shaft (240) extends cutter (260F) beyond lateral side (108C) and cutter (260S) beyond lateral side (108A) of implant (100).

Figure 6:
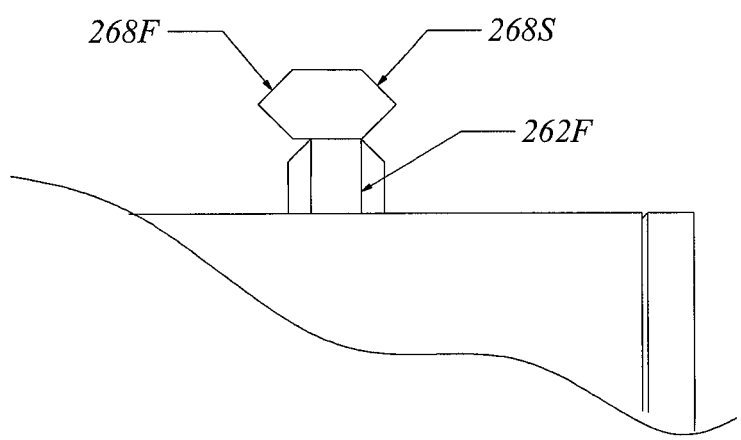
FIG. 6 is a frontal view of a preferred embodiment of cutter (260F) shown in FIG. 5 as seen from the anterior side of implant (100).

FIG. 6 is a frontal view of a preferred embodiment of cutter (260F) shown in FIG. 5 as seen from the anterior side of implant (100). Cutter (260F) is provided with first and second cutting blades (268F, 268S) that allow cutter (260F) to cut in both the clockwise and counterclockwise directions. Depending on engineering parameters cutters (260F, 260S) can be equipped with one or more cutting blades. Along with the cutting function of cutters (260F, 260S), near the conclusion of the surgical procedure, cutting blades (268F, 268S) can be rotated to cut into bone so that cutters (260F, 260S) further anchor the implant (100) within the joint space.

Figure 7:
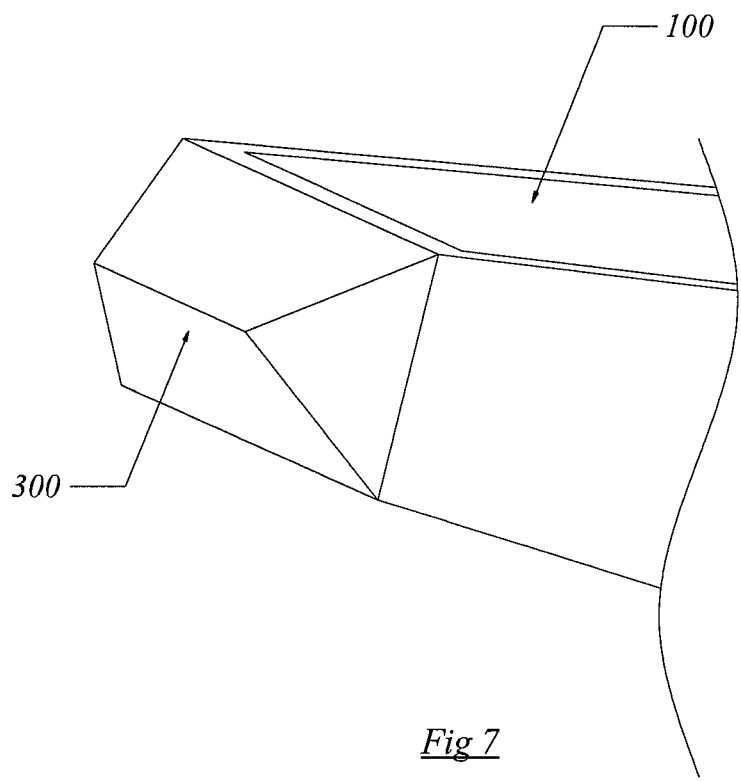
FIG. 7 is a perspective of a preferred embodiment of cutting edge (300) of implant (100).

FIG. 7 is a perspective of cutting edge (300) of implant (100). Cutting edge (300) can be integral with implant (100) or cutting edge (300) can be manufactured as an interchangeable fitting for implant (100). Within the ambit of the current joint arthrodesis system, cutting edges (300) are capable of dissecting through adipose, muscle and/or joint capsule tissues.

Figure 8:
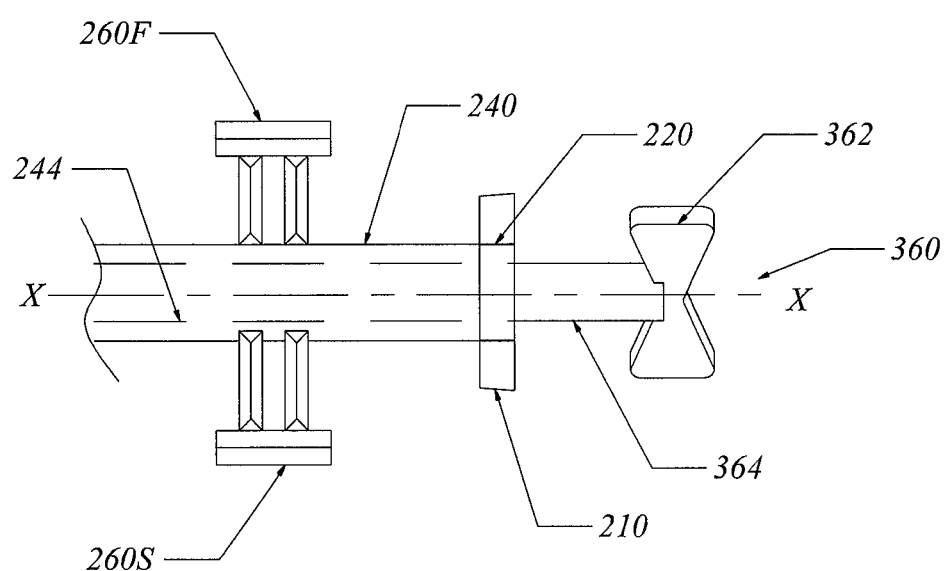
FIG. 8 is a lateral view as seen from side (108B) with lateral sides (108A-D) of implant (100) cut away.

FIG. 8 is a lateral view as seen from side (108B) with sides (108A-D) of implant (100) cut away. Plate (210) includes aperture (220) capable of receiving hand tool (360). Hand tool (360) includes handle (362) and stem (364) that extends from handle (362). Shaft (240) includes receptacle (244) for reciprocating with stem (364) of hand tool (360). Interaction between stem (364) and receptacle (244) allows hand tool (360) to rotate cutters (260F, 260S) in both clockwise and counterclockwise directions. In select preferred embodiments receptacle (244) can extend the entire length of (240) for allowing ingress and egress of surgical appliances and instruments from the surgical field, e.g., wires, cannulas, vacuum tubes, fiber optics, etc.

Figure 9:
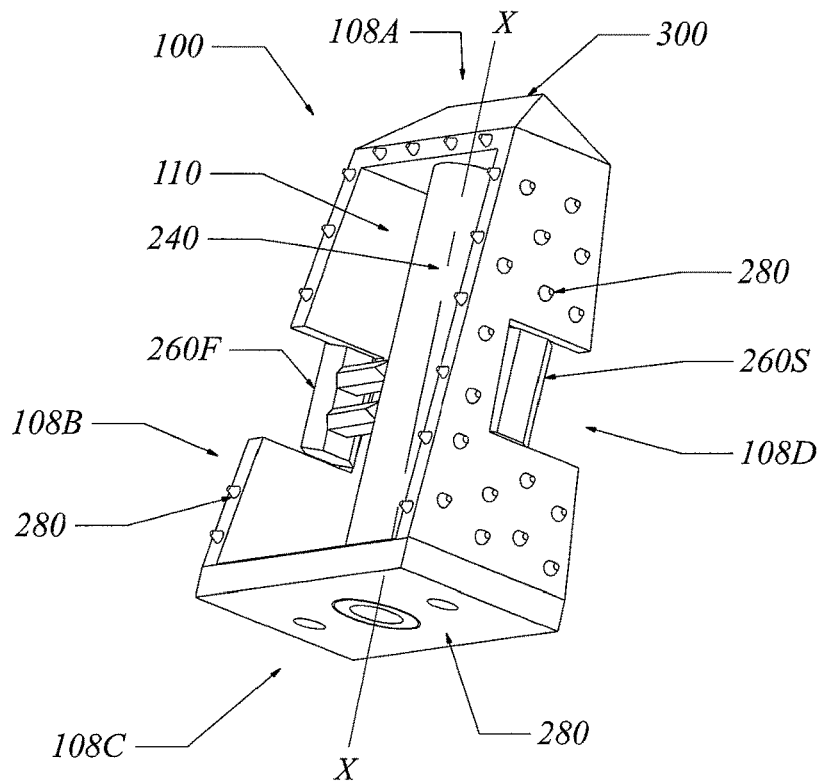
FIG. 9 is a perspective of a preferred embodiment of implant (100).

FIG. 9 is a perspective of a preferred embodiment of implant (100) that depicts cutting edge (300), rotatable cutters (260F, 260S) and opening (110) of implant (100). As shown, barbs (280) extend away from surfaces of lengthwise sides (108B, 108C, 108D). It is believed that barbs (280) can assist in deterring movement of implant (100) within the joint space.

Figure 10:
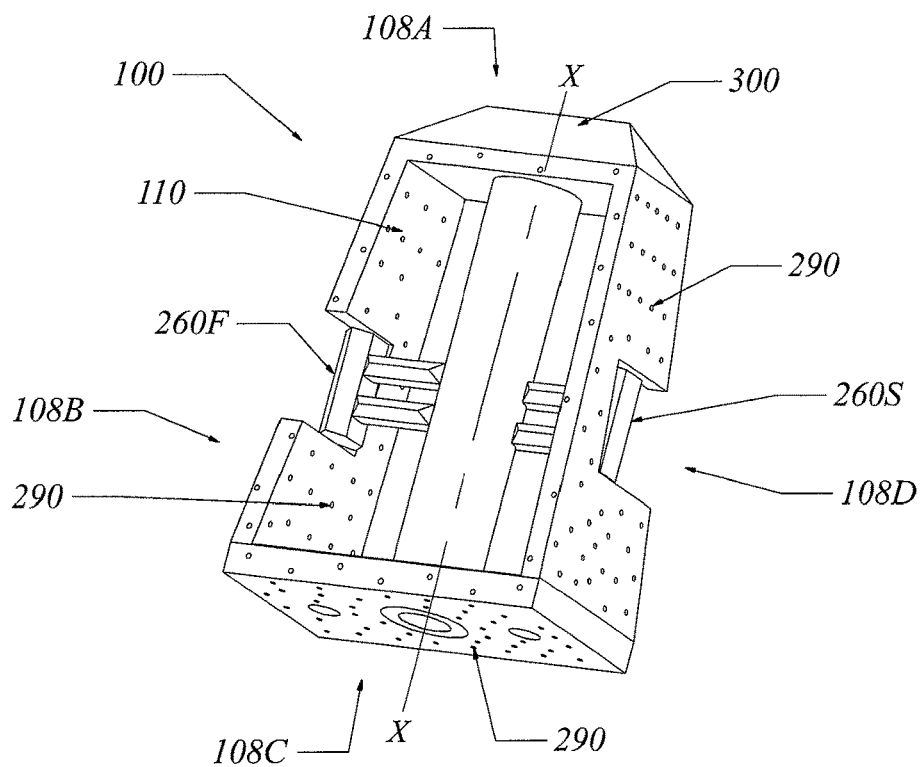
FIG. 10 is a perspective of a preferred embodiment of implant (100).

FIG. 10 is a perspective of a preferred embodiment of implant (100) that depicts cutting edge (300), rotatable cutters (260F, 260S) and opening (110) of implant (100). In the FIG. 10 embodiment, surfaces of sides (108B, 108C, 108D) are provided with micropores (290) of various volumes. It is believed that surface micropores (290) can assist with long term fixation of the implant by allowing more bone ingrowth into the implant. In accordance with the FIG. 10 preferred embodiment of spinal implant (100), micropores (290) are generated by surface treatments to at least a portion of surfaces of sides (108B, 108C, 108D). Micropores (290) can be created by abrasive, chemical or laser means.

Figure 11:
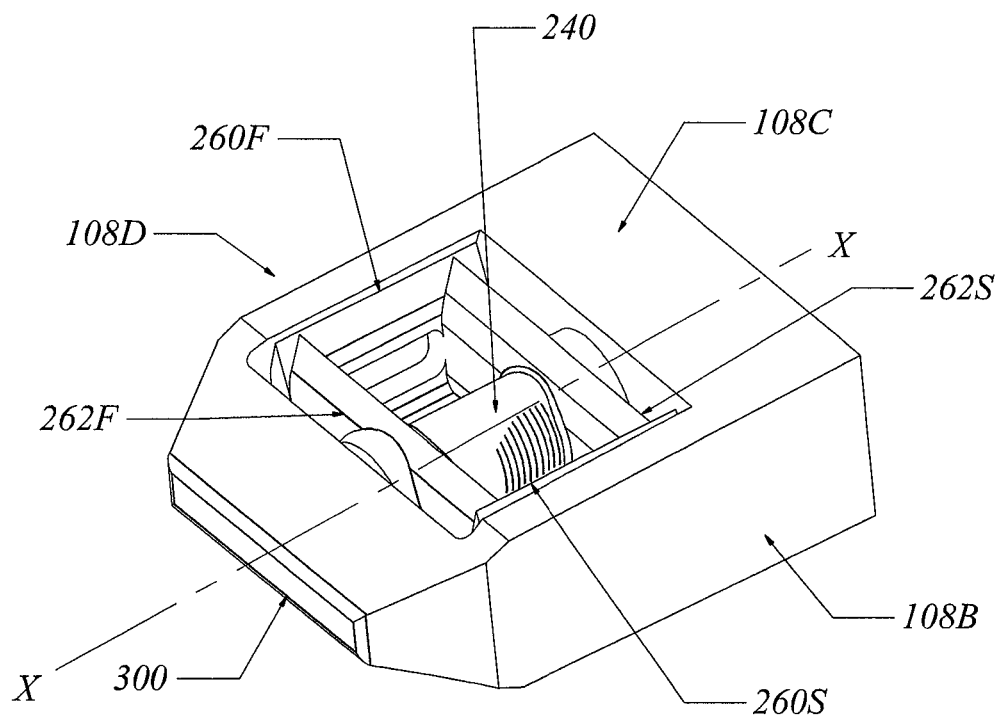
FIG. 11 is a perspective of a preferred embodiment of implant (100) where cutters (260F, 260S) are capable of being rotated 360 degrees about longitudinal axis X-X.

FIG. 11 is a perspective of a preferred embodiment of implant (100) where cutters (260F, 260S) are capable of being rotated 360 degrees about longitudinal axis X-X.

Figure 12:
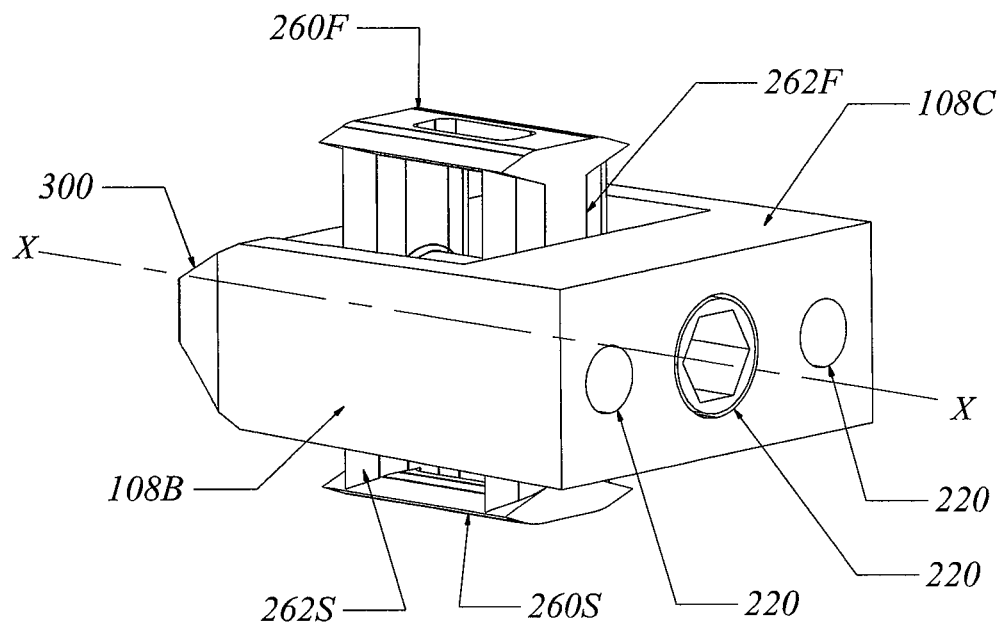
FIG. 12 is a perspective of a preferred embodiment of implant (100) where cutters (260F, 260S) are capable of being rotated 360 degrees about longitudinal axis X-X.

FIG. 12 is another perspective of a preferred embodiment of implant (100) where cutters (260F, 260S) are capable of being rotated 360 degrees about longitudinal axis X-X.

As measured along longitudinal axis X-X of implant's (100) framework, preferred embodiments are provided with cutting edge (300) that can be up to about 3 millimeters in length. The length of implant (100), including cutting edge (300) can be from about 6 millimeters to about 50 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

Figure 13:
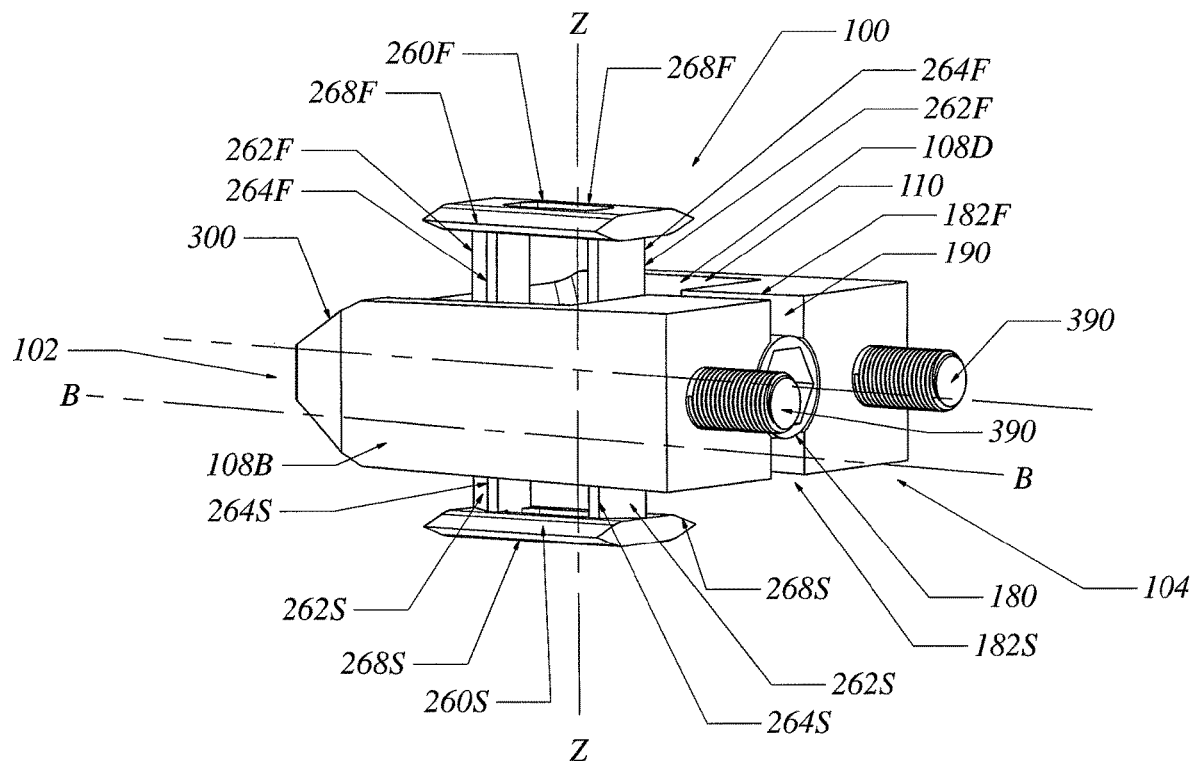
FIG. 13 is a perspective of a preferred embodiment of implant (100) where cutters (260F, 260S) extend beyond opening (110).
Figure 14:
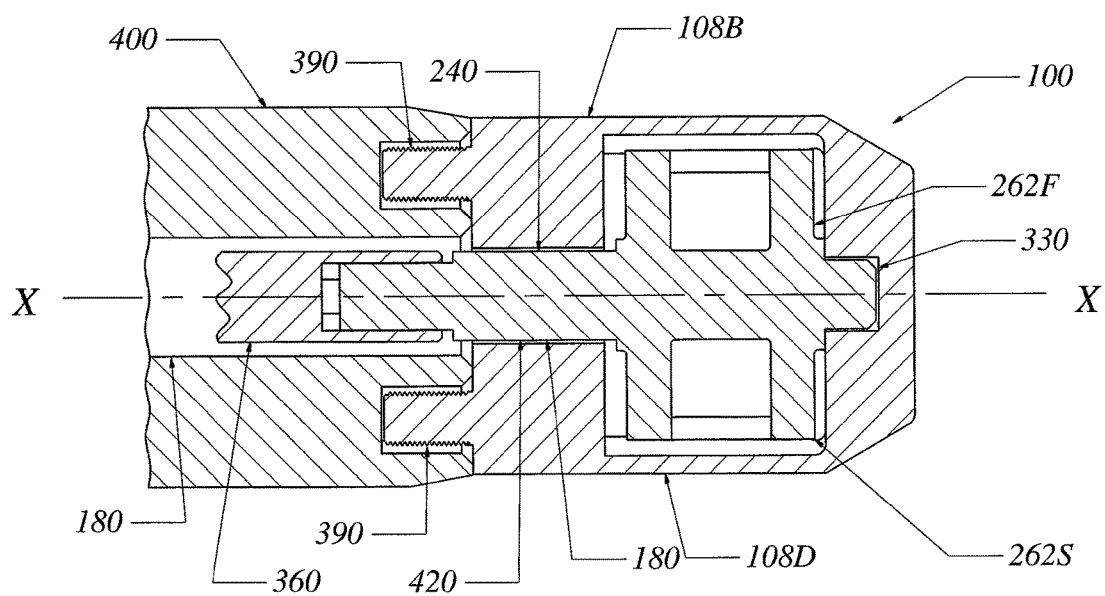
FIG. 14 is a top planar view of section B-B of FIG. 13, where cutters (260F, 260S) of implant (100) do not extend beyond opening (110).

With reference to FIGS. 13 and 14, a preferred embodiment of implant (100) is enabled. Implant (100) is provided with a biocompatible construction including a longitudinal axis X-X that can be measured in a coexisting or parallel direction of a longest dimension of the biocompatible construction. In selected preferred embodiments, when engineering parameters require, longitudinal axis X-X can be offset from center. Superior opening (110) and opposed inferior opening (not shown in FIG. 13) are positioned outward from implant's longitudinal axis X-X.

Implant (100) includes anterior side (102), posterior or surgeon facing side (104) and lateral sides (108B, 108D) extending between anterior side (102) and surgeon facing side (104). Anterior side (102) of implant (100) is provided with cutting edge (300) on the outward face of anterior side (102) and socket (330) on the inward face of anterior side (102). Surgeon facing side (104) is provided with a bearing (180) and at least one connector (390) adapted to engage an insertion device (400). In the FIGS. 13 and 14 preferred embodiment of implant (100), surgeon facing side (104) is provided with gaps (182F, 182S) creating pathway (190) through bearing (180) of posterior side (104).

As shown, rotatable shaft (240) extends along longitudinal axis X-X from anterior socket (330) through bearing (180). However, in other preferred embodiments, rotatable shaft (240) can contact bearing (180) without extending through bearing (180). Arms (262F, 262S) are connected to rotatable shaft (240) and support cutters (260F, 260S). Blades (268F, 268S) associated with cutters (260F, 260S) are adapted to cut when rotated in a clockwise or counterclockwise direction when shaft (240) is rotated. Sharp edges (264F, 264S) of arms (262F, 262S) can be adapted to remove cartilage, expose subcortical bone and/or morselize graft material. Tool (360) can be used to rotate shaft (240). In select preferred embodiments anterior side (102) is of lesser cross-sectional area than surgeon facing side (104).

Regarding the preferred embodiment of the current implant enabled in FIGS. 13 and 2, when surgical conditions require shaft (240) can be moved longitudinally along axis X-X and shaft (240) can be detached/reattached from socket (330). When medically required, rotation of shaft (240) positions arms (262F, 262S) such that shaft (240) can be detached from socket (330) and arms (262F, 262S) can be pulled through pathway (190).

With a view toward to FIGS. 13 and 14 and within the scope of the current invention, preferred embodiments of joint implant (100) can have a length greater than a width. In select preferred embodiments, the width of joint implant (100) is greater than the height of joint implant (100). In other preferred embodiments of joint implant (100), the height of implant (100) is greater than the width of joint implant (100). The inward sides of anterior side (102), posterior side (104) and lengthwise sides (108B and 108D)

facing longitudinal axis X-X create an available inner volume of implant (100) which can receive osteogenic as well as other substances.

As measured along longitudinal axis X-X of implant's (100) biocompatible construction, preferred embodiments are provided with cutting edge (300) that can be up to about 3 millimeters in length. The length of implant (100), including cutting edge (300) can be from about 6 millimeters to about 50 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

With respect to this application and in view FIGS. 13 and 14, the longitudinal axis of joint implant (100) is measured along axis X-X. Axis X-X can correspond with shaft (240) or in some preferred embodiments, shaft (240) can be offset from axis X-X. Width of implant (100) is measured along axis Y-Y or an axis parallel to axis Y-Y shown in FIG. 13. Height of joint implant is measured along axis Z-Z or an axis parallel to axis Z-Z of the joint implant's biocompatible construction.

Figure 15:
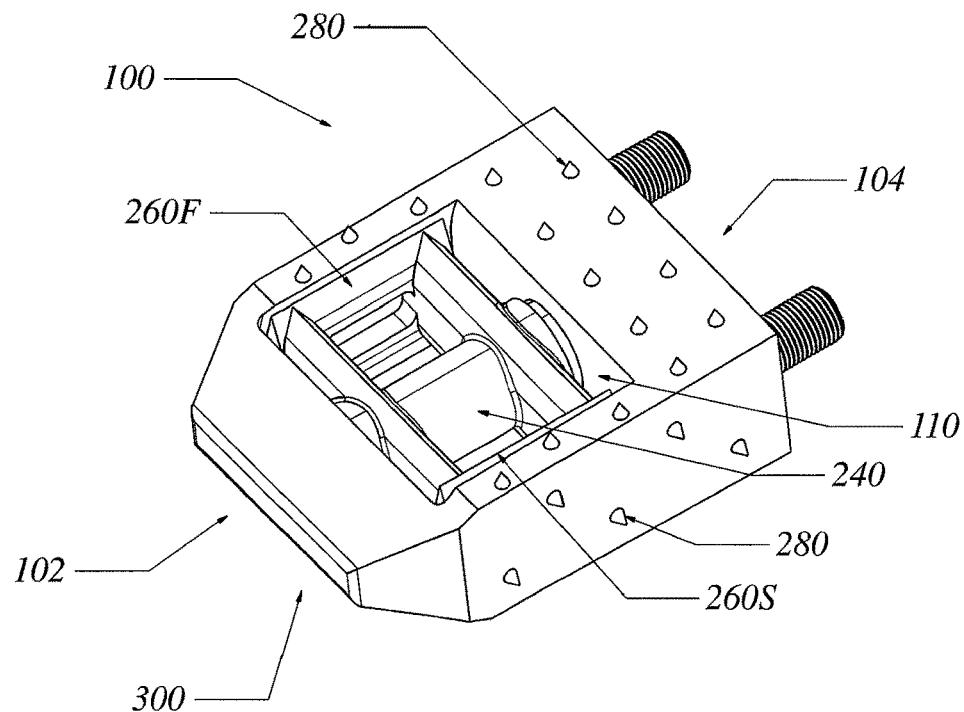
FIG. 15 is a perspective of a preferred embodiment of implant (100) where cutters (260F, 260S) extend beyond opening (110).

FIG. 15 is a perspective of a preferred embodiment of implant (100) that includes barbs.

Figure 16:
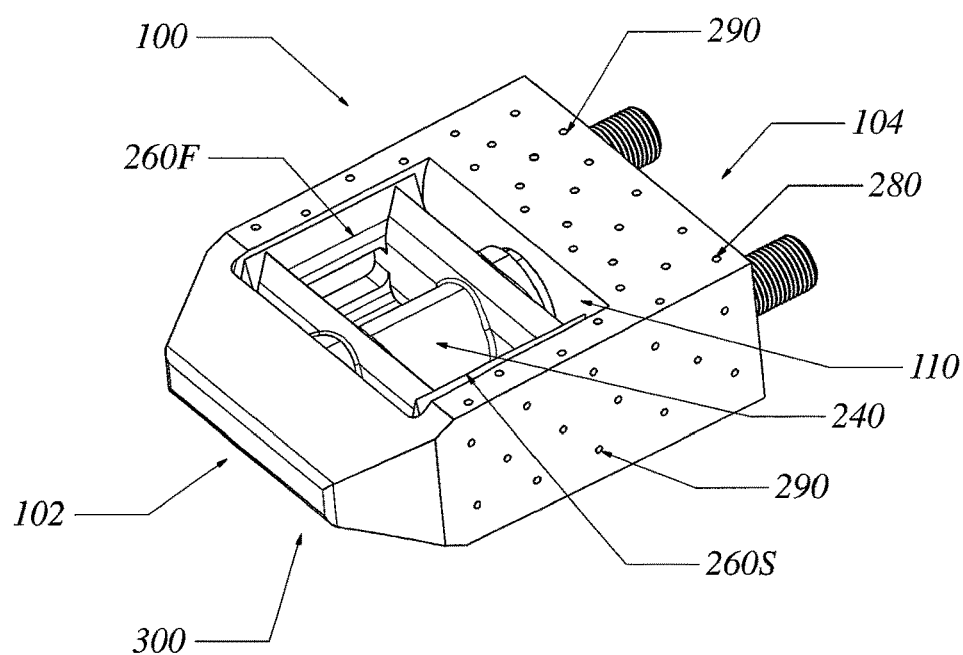
FIG. 16 is a top planar view of section B-B of FIG. 15, where cutters (260F, 260S) of implant (100) do not extend beyond opening (110).

FIG. 16 is a perspective of a preferred embodiment of implant (100) that includes surface treatments.

Figure 17:
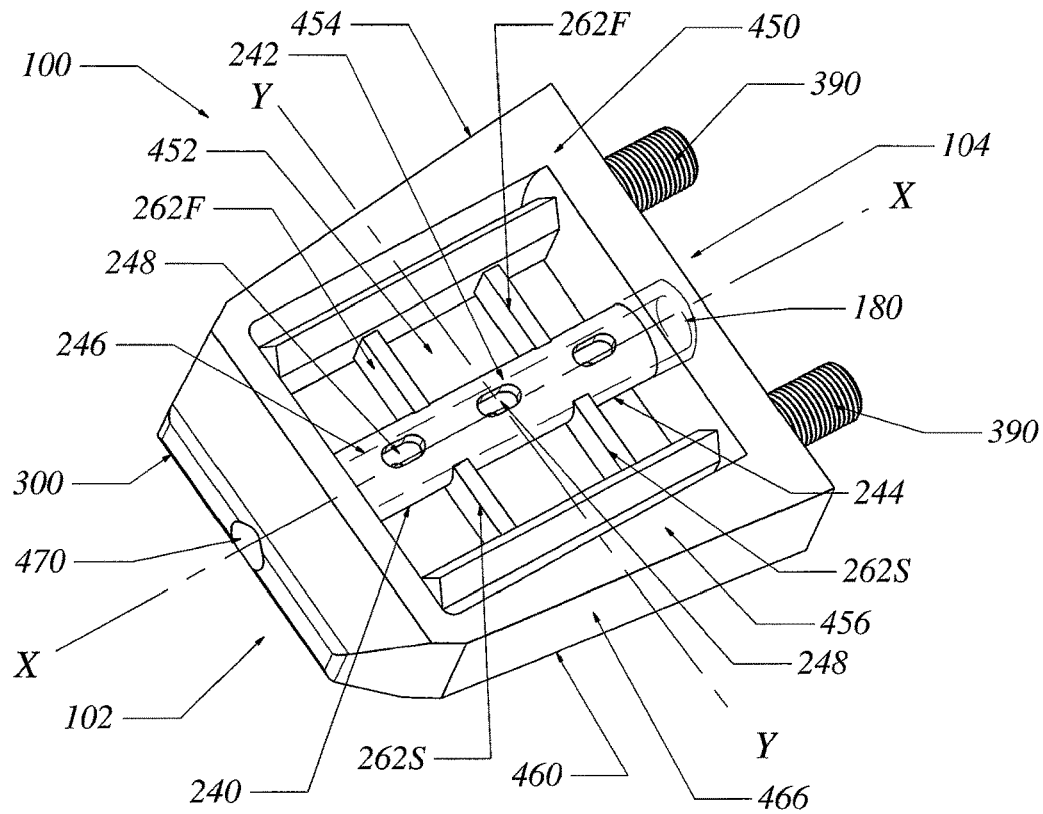
FIG. 17 is a perspective of a preferred embodiment of implant (100).
Figure 18:
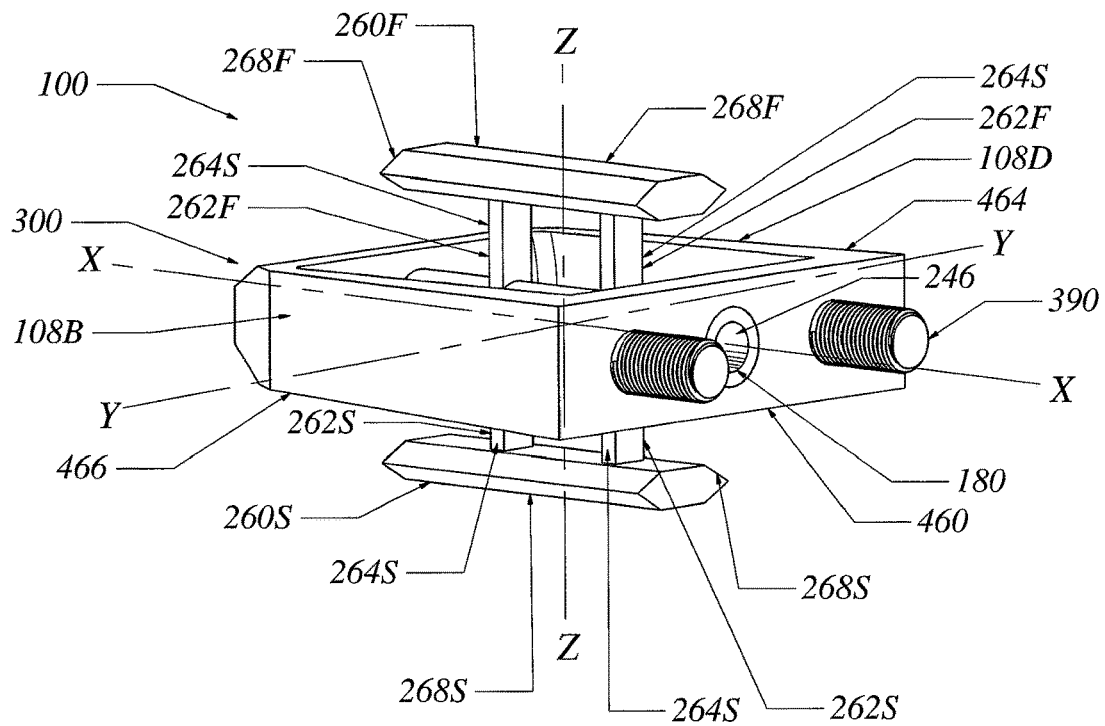
FIG. 18 is a perspective of a preferred embodiment of implant (100).

With reference to FIGS. 17 and 18, a preferred embodiment of implant (100) is enabled. Implant (100) is provided with a biocompatible construction including a longitudinal axis X-X that can be measured in a coexisting or parallel direction of a longest dimension of the biocompatible construction. In selected preferred embodiments, when engineering parameters require, longitudinal axis X-X can be offset from center.

Implant (100) is provided with first trapezoidal surface (450) and opposed trapezoidal surface (460). First trapezoidal surface (450) includes aperture (452) and two margins (454, 456) of equal length. Second trapezoidal surface (460) includes aperture (462) and two margins (464, 466) of equal length. Implant (100) also includes anterior side (102), posterior or surgeon facing side (104) and lateral sides (108B, 108D) extending between anterior side (102) and surgeon facing side (104). Anterior side (102) and surgeon facing side (104) extend between first trapezoidal surface (450) and second trapezoidal surface (460). Anterior side (102) of implant (100) is provided with cutting edge (300) on the outward face of anterior side (102).

Orifice (470) extends through cutting edge (300) and anterior side (102). Among other things, orifice (470) allows access of a guide wire (not shown in FIGS. 17-18) when medically required. Other preferred embodiments of the current invention do not include orifice (470). Surgeon facing side (104) is provided with a bearing (180) and at least one connector (390) adapted to engage an insertion device (not shown in FIGS. 17 and 18).

As shown, rotatable shaft (240) extends along longitudinal axis X-X from orifice (470) into bearing (180). However, in other preferred embodiments, rotatable shaft (240) can contact bearing (180) and extend through bearing (180).

Rotatable shaft (240) includes conduit (242) extending through the length of shaft (240). Conduit (242) is defined by the inward face (246) of shaft's (240) cylindrical wall (244). One or more windows (248) are positioned in cylindrical wall (240). Each window (248) is adapted to expose conduit (242) the surgical created cavity external from joint implant (100). Conduit (242) can carry one or more substances that diffuse through windows (240) into the surround surgically created cavity (not shown in FIGS. 17 and 18).

Arms (262F, 262S) are connected to rotatable shaft (240) and support cutters (260F, 260S). Blades (268F, 268S) associated with cutters (260F, 260S) are adapted to cut when rotated in a clockwise or counterclockwise direction when shaft (240) is rotated. Sharp edges (264F, 264S) of arms (262F, 262S) can be adapted to remove cartilage, expose subcortical bone and/or morselize graft material. Tool (360) as shown in FIG. 14 can be used to rotate shaft (240). In select preferred embodiments anterior side (102) is of lesser cross-sectional area than surgeon facing side (104).

With a view toward to FIGS. 17 and 18 and within the scope of the current invention, preferred embodiments of joint implant (100) can have a length greater than a width. In select preferred embodiments, the width of joint implant (100) is greater than the height of joint implant (100). In other preferred embodiments of joint implant (100), the height of implant (100) is greater than the width of joint implant (100). The inward sides of anterior side (102), posterior side (104) and margins (454, 456, 464, 466) facing longitudinal axis X-X create an available inner volume of implant (100) which can receive osteogenic as well as other substances.

As measured along longitudinal axis X-X of implant's (100) biocompatible construction, preferred embodiments are provided with cutting edge (300) that can be up to about 3 millimeters in length. The length of implant (100), including cutting edge (300) can be from about 6 millimeters to about 50 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

With respect to this application and in view FIGS. 17 and 18, the longitudinal axis of joint implant (100) is measured along axis X-X. Axis X-X can correspond with shaft (240) or in some preferred embodiments, shaft (240) can be offset from axis X-X. Width of implant (100) is measured along axis Y-Y or an axis parallel to axis Y-Y shown in FIGS. 17 and 18. Height of joint implant is measured along axis Z-Z or an axis parallel to axis Z-Z of the joint implant's biocompatible construction.

Figure 19:
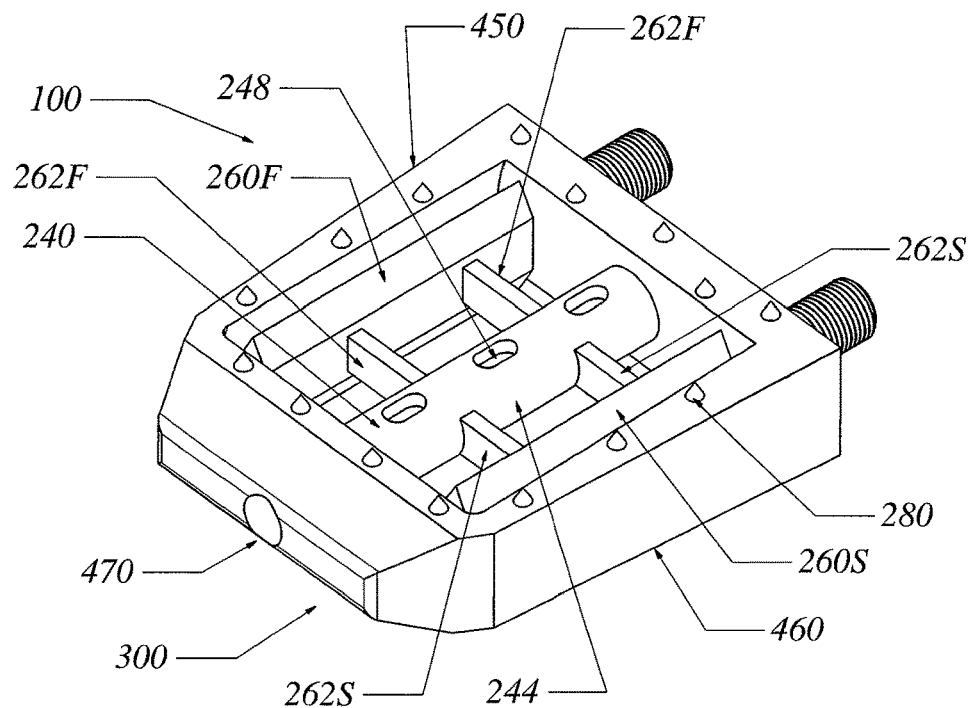
FIG. 19 is a perspective of a preferred embodiment of implant (100) that includes barbs.

FIG. 19 is a perspective of a preferred embodiment of implant (100) that includes barbs.

Figure 20:
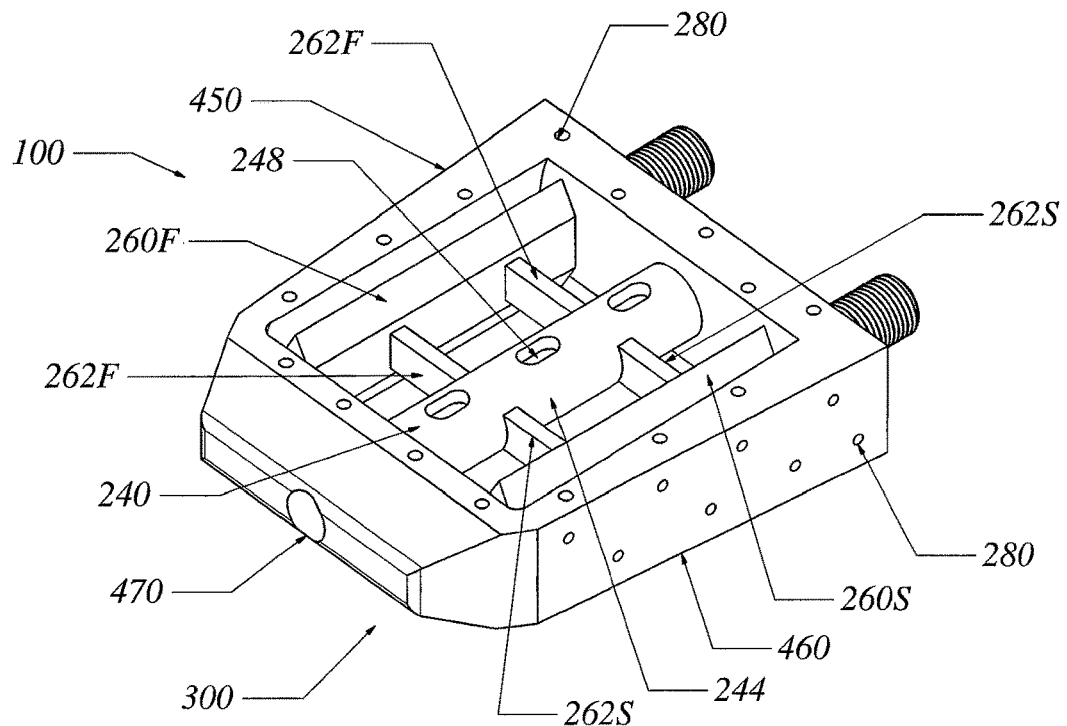
FIG. 20 is a perspective of a preferred embodiment of implant (100) that includes surface treatments.

FIG. 20 is a perspective of a preferred embodiment of implant (100) that includes surface treatments.

Within the scope of the current invention, surface treatments can include barbs (280), micropores (290) or metal or abrasive particles incorporated into or onto the biocompatible composition.

Select preferred embodiments of the current invention have been disclosed and enabled as required by Title 35 of the United States Code.

What is claimed is:

1. A joint implant comprising a framework; said framework comprising:
   a) a longitudinal axis measured in a coexisting or parallel direction of a longest dimension of said framework;
   b) openings outward from said longitudinal axis;
   c) an anterior side comprising a cutting edge;
   d) a surgeon facing side at an end opposite said anterior side; said surgeon facing side comprising one or more apertures;
   e) a rotatable shaft extending about said longitudinal axis and-between said anterior side and said surgeon facing side;

f) a first arm connected with a first side of said shaft; said first arm supporting a first cutter comprising one or more blades, wherein on clockwise or counterclockwise rotation of said shaft, said blades are capable of cutting in a 360 degree radial path; and g) a second arm connected with a second side of said shaft; said second arm supporting a second cutter comprising one or more blades, wherein on clockwise or counterclockwise rotation of said shaft, said blades are capable of cutting in the 360 degree radial path.

2. The joint implant of claim 1: said framework comprising first and second lateral sides connected with said anterior side and said surgeon facing side, wherein said framework includes a length greater than a width.

3. The joint implant of claim 2, wherein one or more surfaces of said framework comprise surface treatments and said framework's anterior side has a lesser cross-sectional area than a cross-sectional area of said surgeon facing side.

4. The joint implant of claim 3, wherein said first arm and said second arm comprise one or more sharp edges adapted to remove cartilage, expose subcortical bone and morselize graft material.

5. The joint implant of claim 4 further comprising one or more connectors connected to said surgeon facing side, wherein each said connector is adapted to engage a device.

6. A joint implant comprising a framework; said framework comprising:
  a) a longitudinal axis measured in a coexisting or parallel direction of a longest dimension of said framework;
  b) openings outward from said longitudinal axis;
  c) an anterior side comprising a cutting edge;
  d) a surgeon facing side at an end opposite said anterior side; said surgeon facing side comprising at least one aperture;
  e) a rotatable shaft extending along said longitudinal axis and between said anterior side and said surgeon facing side;
  f) first and second arms connected to different sides of said shaft; said first and second arms supporting first and second cutters comprising one or more blades, wherein on rotation of said shaft, said first and second arms are capable of rotating in a 360 degree path; and
  g) one or more connectors connected to said surgeon facing side, wherein each said connector is adapted to engage a device.

7. The joint implant of claim 6: said framework comprising first and second lateral sides connected with said anterior side and said surgeon facing side, wherein said framework includes a length greater than a width.

8. The joint implant of claim 7, wherein one or more surfaces of said framework comprise surface treatments and said framework's anterior side has a lesser cross-sectional area than a cross-sectional area of said surgeon facing side.

9. The joint implant of claim 8, wherein said first and second arms comprise one or more sharp edges adapted to remove cartilage, expose subcortical bone and morselize graft material.

10. A joint implant comprising a biocompatible construction with a longitudinal axis measured in a coexisting or parallel direction of a longest dimension of the biocompatible construction; said biocompatible construction comprising:
  a) openings outward from said longitudinal axis;
  b) an anterior side comprising:
    i) an outward cutting edge; and
    ii) an inward socket;
  c) a surgeon facing side, opposite said anterior side, comprising a bearing comprising opposed first and second gaps perpendicular to said longitudinal axis;
  d) a rotatable shaft engaging said socket and extending along said longitudinal axis from said socket through said bearing, wherein said rotatable shaft is detachable from said socket and said bearing; and
  e) first and second arms connected with said shaft; said first and second arms supporting first and second cutters comprising one or more blades, wherein on rotation of said shaft, said blades are adapted to cut in a clockwise or counterclockwise direction.

11. The joint implant of claim 10: said biocompatible construction comprising first and second lateral sides connected with said anterior side and said surgeon facing side, wherein said biocompatible construction includes a length greater than a width.

12. The joint implant of claim 11, wherein:
  a) said rotatable shaft's diameter engaging said socket is less than said shaft's diameter proximate said bearing; and
  b) said biocompatible construction's anterior side has a lesser cross-sectional area than a cross-sectional area of said surgeon facing side.

13. The joint implant of claim 12 comprising one or more connectors connected to the surgeon facing side, wherein each connector is adapted to engage a device.

14. The joint implant of claim 13, wherein:
  a) said first and second arms comprise one or more sharp edges adapted to remove cartilage, expose subcortical bone and/or morselize graft material; and
  b) one or more surfaces of said biocompatible construction comprise surface treatments.

15. A joint implant comprising a biocompatible construction with a longitudinal axis spanning a longest dimension of said biocompatible construction; said biocompatible construction comprising:
  a) openings outward from said longitudinal axis;
  b) an anterior side comprising:
    i) a cutting edge; and
    ii) an inward socket;
  c) a surgeon facing side comprising a bearing comprising first and second gaps;
  d) a rotatable shaft, extending along or parallel to said longitudinal axis, engaging said socket and said bearing, wherein said rotatable shaft is detachable from said biocompatible construction; and
  e) first and second arms connected with said shaft; said first and second arms supporting first and second cutters comprising one or more blades, wherein on rotation of said shaft, said blades are adapted to cut in a clockwise or counterclockwise direction.

16. The joint implant of claim 15: said biocompatible construction comprising first and second lateral sides connected with said anterior side and said surgeon facing side, wherein said biocompatible construction includes a length greater than a width.

17. The joint implant of claim 16, wherein:
  a) said rotatable shaft's diameter engaging said socket is less than said shaft's diameter proximate said bearing;
  b) said first and second gaps are perpendicular to said longitudinal axis; and
  c) said biocompatible construction's anterior side has a lesser cross-sectional area than a cross-sectional area of said surgeon facing side.

18. The joint implant of claim 17 comprising one or more connectors connected to the surgeon facing side, wherein each connector is adapted to engage a device.

19. The joint implant of claim 18, wherein:
a) said first and second arms comprise one or more sharp edges adapted to remove cartilage, expose subcortical bone and/or morselize graft material; and
b) one or more surfaces of said biocompatible construction comprise surface treatments.

20. A joint implant comprising a biocompatible construction with a longitudinal axis spanning a longer dimension of said biocompatible construction; said biocompatible construction comprising:
a) openings outward from said longitudinal axis;
b) an anterior side comprising:
  i) a cutting edge; and
  ii) a socket;
c) a surgeon facing side comprising a bearing;
d) a rotatable shaft, extending along said longitudinal axis, engaging said socket and said bearing, wherein said rotatable shaft is detachable from said biocompatible construction; and
e) first and second arms, capable of rotating in a 360 degree path, connected with said shaft; said first and second arms supporting first and second cutters comprising one or more blades.

21. The joint implant of claim 20, wherein said bearing comprises first and second gaps creating a pathway for detaching said rotatable shaft from said biocompatible construction.

22. The joint implant of claim 21: said biocompatible construction comprising first and second lateral sides connected with said anterior side and said surgeon facing side, wherein said biocompatible construction includes a length greater than a width.

23. The joint implant of claim 22, wherein:
a) said rotatable shaft's diameter engaging said socket is less than said shaft's diameter proximate said bearing;
b) said first and second gaps are perpendicular to said longitudinal axis; and
c) said biocompatible construction's anterior side has a lesser cross-sectional area than a cross-sectional area of said surgeon facing side.

24. The joint implant of claim 23 comprising one or more connectors connected to the surgeon facing side, wherein each connector is adapted to engage a device.

25. The joint implant of claim 24, wherein:
a) said first and second arms comprise one or more sharp edges adapted to remove cartilage, expose subcortical bone and/or morselize graft material; and
b) one or more surfaces of said biocompatible construction comprise surface treatments.

26. A joint implant comprising a biocompatible construction with a longitudinal axis spanning a longer dimension of said biocompatible construction; said biocompatible construction comprising:
a) a first trapezoidal surface comprising a first aperture therein and a first two margins of equal length;
b) a second trapezoidal surface opposed from said first trapezoidal surface; said second trapezoidal surface comprising a second aperture therein and a second two margins of equal length;
c) an anterior side extending between said trapezoidal surfaces; said anterior side comprising a cutting edge and an orifice extending through said anterior side and said cutting edge;
d) a surgeon facing side comprising a bearing; said surgeon facing side extending between said trapezoidal surfaces; and
e) a rotatable shaft extending from said orifice into said bearing; said rotatable shaft comprising:
  i) a conduit extending through a length of said rotatable shaft; said conduit defined by an inward face of said rotatable shaft's cylindrical wall;
  ii) one or more windows, positioned on said cylindrical wall; each window exposing said conduit to a surgically created cavity external from said joint implant; and
  iii) first and second arms connected with said rotatable shaft; said first and second arms supporting first and second cutters comprising one or more blades, wherein on rotation of said shaft, said blades are adapted to cut in a clockwise or counterclockwise direction.

27. The joint implant of claim 26, wherein said biocompatible construction includes a length greater than a width.

28. The joint implant of claim 27 comprising one or more connectors connected to said surgeon facing side, wherein each connector is adapted to engage a device.

29. The joint implant of claim 28, wherein one or more surfaces of said biocompatible construction comprise surface treatments.

30. The joint implant of claim 29, wherein said first and second arms comprise one or more sharp edges adapted to remove cartilage, expose subcortical bone and/or morselize graft material.

31. A joint implant comprising a biocompatible construction with a longitudinal axis spanning a longer dimension of said biocompatible construction; said biocompatible construction comprising:
a) openings outward from said longitudinal axis;
b) an anterior side comprising a cutting edge extending forward from said anterior side and an orifice extending through said anterior side and said cutting edge;
c) a surgeon facing side comprising a bearing, wherein said anterior side has a lesser cross-sectional area than a cross-sectional area of said surgeon facing side; and
d) a shaft, rotatable in a clockwise or counterclockwise direction, extending from said orifice into said bearing; said shaft comprising:
  i) a conduit extending through a length of said shaft and connected with said orifice; said conduit defined by an inward face of said shaft's cylindrical wall;
  ii) one or more windows, positioned on said cylindrical wall; each window exposing said conduit to a surgically created cavity external from said joint implant; and
  iii) first and second arms connected with said shaft; said first and second arms supporting first and second cutters comprising one or more blades.

32. The joint implant of claim 31, wherein said biocompatible construction includes a length greater than a width.

33. The joint implant of claim 32 comprising one or more connectors connected to said surgeon facing side, wherein each connector is adapted to engage a device.

34. The joint implant of claim 33, wherein one or more surfaces of said biocompatible construction comprise surface treatments.

35. The joint implant of claim 34, wherein said first and second arms comprise one or more sharp edges adapted to remove cartilage, expose subcortical bone and/or morselize graft material.

* * * * *